(12) United States Patent
Bystrom et al.

(10) Patent No.: US 6,398,744 B2
(45) Date of Patent: Jun. 4, 2002

(54) PUBLIC ACCESS CPR AND AED DEVICE

(75) Inventors: Steven R. Bystrom; Darren R. Sherman, both of Portola Valley, CA (US)

(73) Assignee: Revivant Corporation, Sunnyvale, CA (US)

( * ) Notice: Subject to any disclaimer, the term of this patent is extended or adjusted under 35 U.S.C. 154(b) by 0 days.

(21) Appl. No.: 09/263,656

(22) Filed: Mar. 5, 1999

(51) Int. Cl.[7] .............................................. A61H 31/00
(52) U.S. Cl. ............................ 601/41; 601/44; 601/152
(58) Field of Search ........................... 601/6, 9, 10, 41, 601/43, 44, 149–152; 434/265

(56) References Cited

U.S. PATENT DOCUMENTS

| | | | | |
|---|---|---|---|---|
| 5,104,374 A | * | 4/1992 | Bishko et al. | |
| 5,507,277 A | * | 4/1996 | Rubsamen et al. | |
| 5,738,637 A | * | 4/1998 | Kelly et al. | 601/41 |
| 5,848,593 A | * | 12/1998 | McGrady et al. | |
| 6,090,056 A | * | 7/2000 | Bystrom et al. | 601/41 |

* cited by examiner

Primary Examiner—Danton D. DeMille
(74) Attorney, Agent, or Firm—K. David Crockett, Esq.; Crockett & Crockett

(57) ABSTRACT

A system for resuscitation of a heart attack victim. The system includes CPR device which compresses the victim's chest, a defibrillator which may be used to defibrillate the patient, and an identification system for identifying the person operating the system. Depending on the identity of the operator, the system permits varying degrees of access to components and enablment of the functions of the various subsystems.

3 Claims, 8 Drawing Sheets

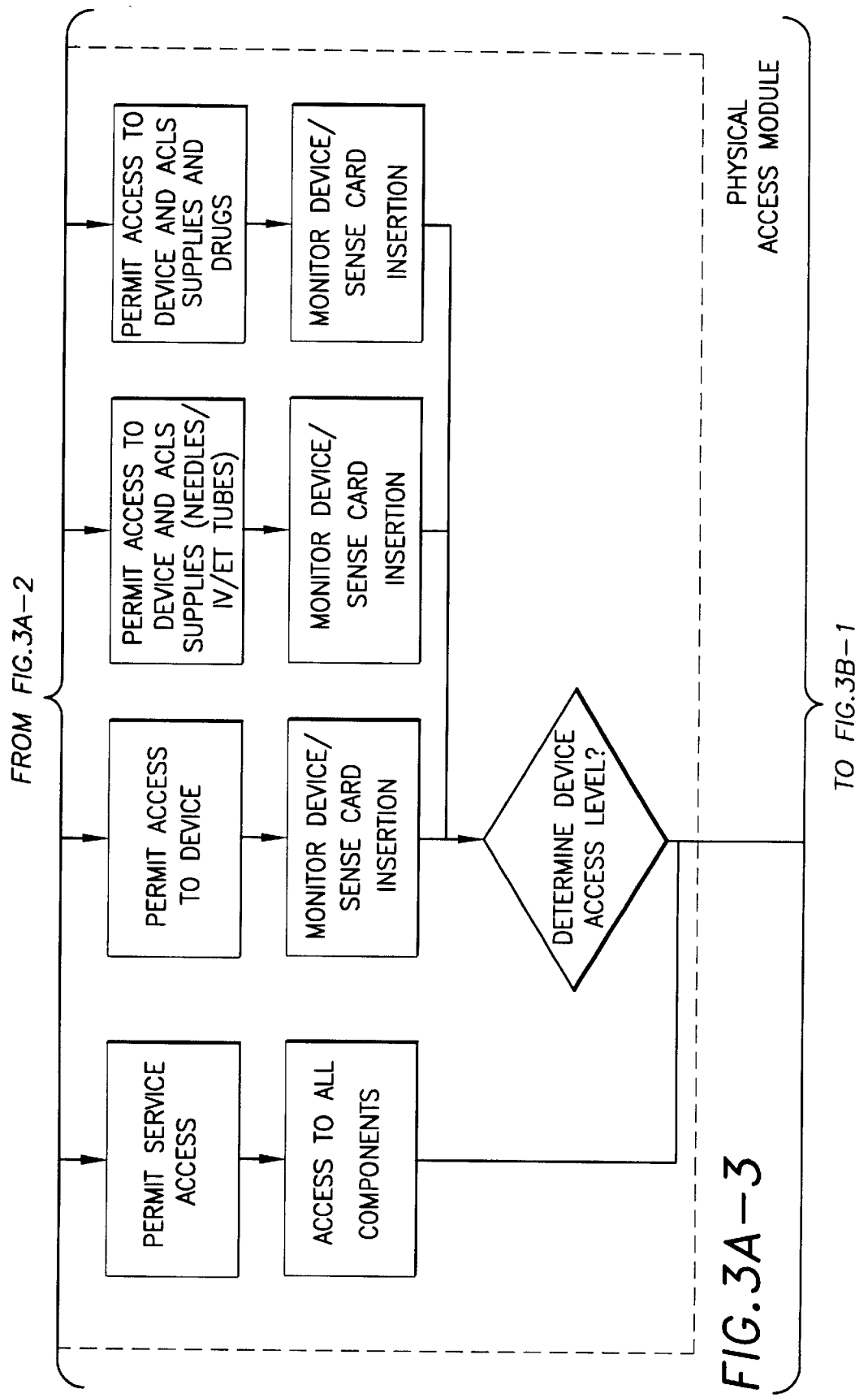

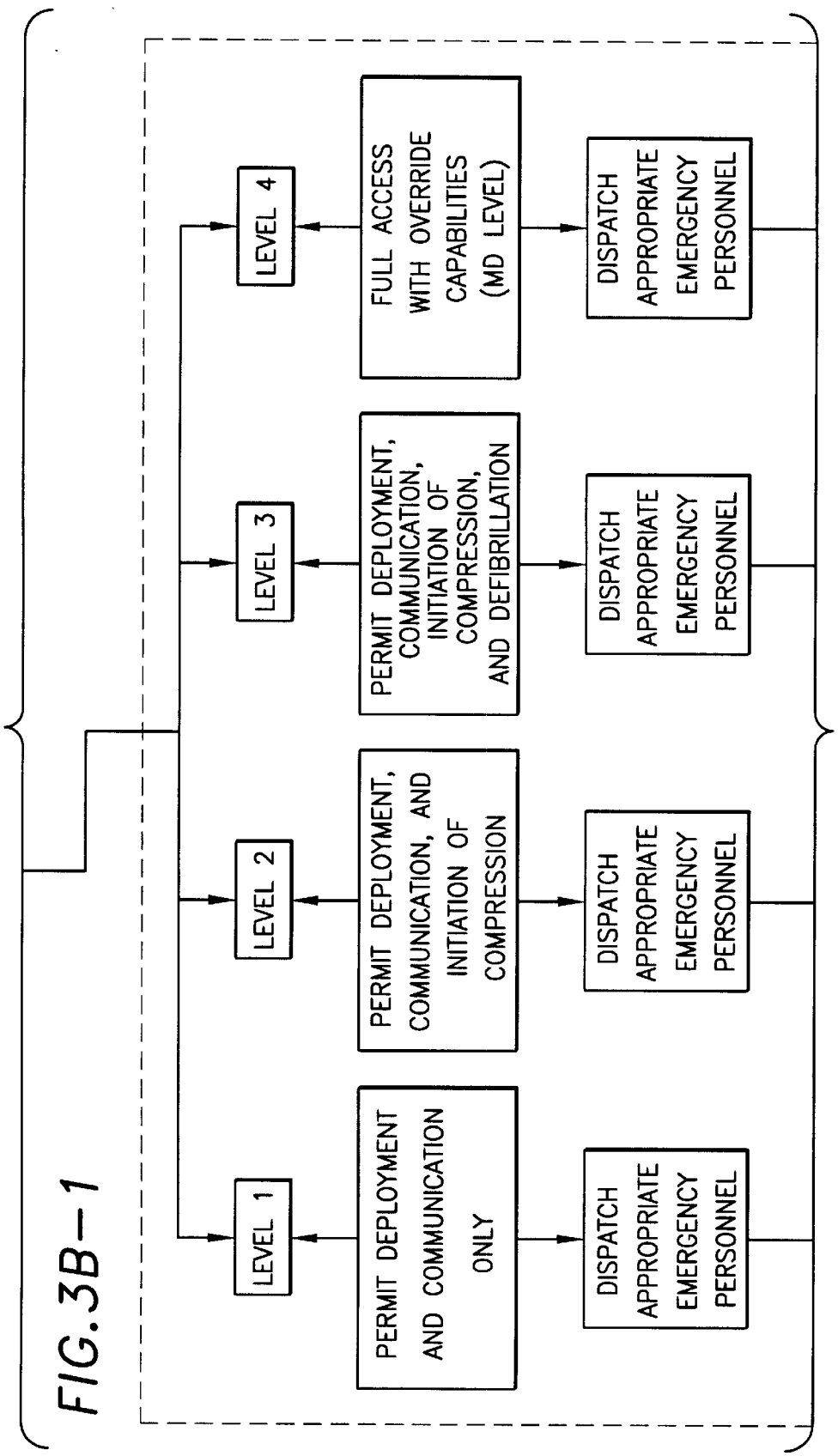

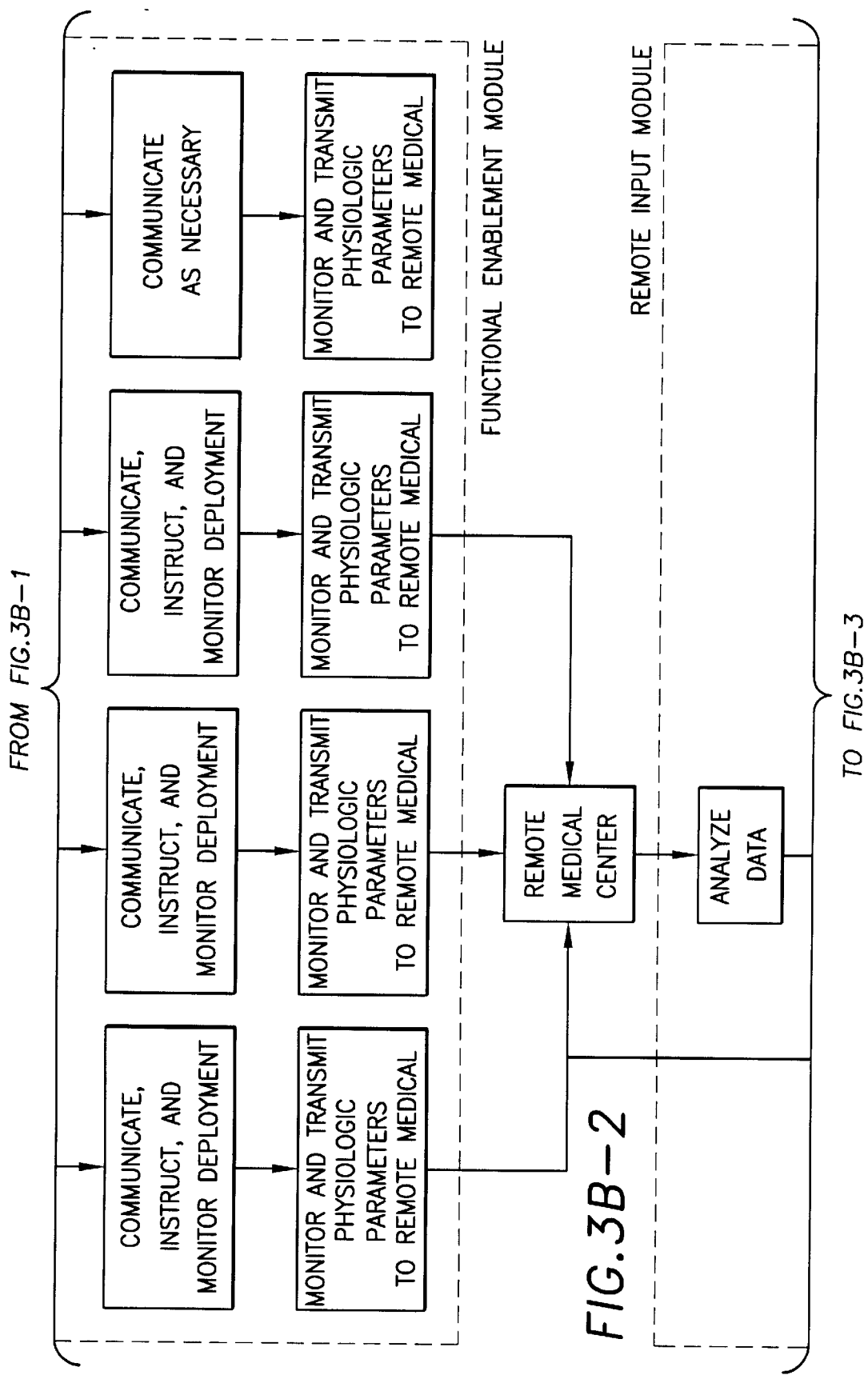

PUBLIC ACCESS CPR AND AED DEVICE

FIELD OF THE INVENTION

This invention relates to the resuscitation of cardiac arrest victims.

BACKGROUND OF THE INVENTION

Cardiopulmonary resuscitation (CPR) is a well known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the victim is not breathing, and mouth to mouth artificial respiration or a bag valve mask is used to supply air to the lungs while the chest compression pumps blood through the body. The methods of providing oxygenated airflow to the lungs are referred to as ventilation.

It has been widely noted that CPR and chest compression can save cardiac arrest victims, especially when applied immediately after cardiac arrest. Chest compression requires that the person providing chest compression repetitively push down on the sternum of the victim at 80–100 compressions per minute. CPR and closed chest compression can be used anywhere, wherever the cardiac arrest victim is stricken. In the field, away from the hospital, CPR may be accomplished by ill-trained by-standers or highly trained paramedics and ambulance personnel.

When a first aid provider performs chest compression well, blood flow in the body is typically about 25–30% of normal blood flow. This is enough blood flow to prevent brain damage. However, when chest compression is required for long periods of time, it is difficult if not impossible to maintain adequate compression of the heart and rib cage. Even experienced paramedics cannot maintain adequate chest compression for more than a few minutes. Hightower, et al., Decay In Quality Of Chest Compressions Over Time, 26 Ann. Emerg. Med. 300 (September 1995). Thus, long periods of CPR, when required, are not often successful at sustaining or reviving the victim. At the same time, it appears that, if chest compression could be adequately maintained, cardiac arrest victims could be sustained for extended periods of time. Occasional reports of extended CPR efforts (45-90 minutes) have been reported, with the victims eventually being saved by coronary bypass surgery. See Tovar, et al., Successful Myocardial Revascularization and Neurologic Recovery, 22 Texas Heart J. 271 (1995).

In efforts to provide better blood flow and increase the effectiveness of bystander resuscitation efforts, chest compression devices capable of performing the tasks of the basic CPR procedure have been proposed and used. Our own modular CPR device, described in our co-pending U.S. patent applications Ser. Nos. 08/922,723 and 09/087,299 provide for circumferential chest compression performed by a battery operated motor and clutch assembly. The chest compressions are accomplished automatically after installation and initialization of the system. The devices are designed for use by both untrained and trained operators, so that they may be used on patients as quickly as possible. It is intended that any bystander recognizing a fallen patient will be able to gain access to a nearby device, install the device, and initiate the operation of the device to commence chest compression and patient monitoring.

Our CPR devices described in our co-pending applications Ser. Nos. 08/922,723 and 09/087,299 also incorporate an automatic emergency defibrillator. Defibrillation is a well known technique for restoring normal heart rhythm to a patient who is in cardiac arrest due to ventricular fibrillation or ventricular tachycardia. It involves attaching electrodes to the patient and applying a large electrical shock to the patient. Defibrillation can resuscitate a large class of cardiac arrest patients, and its success is enhanced by application of the shock early in the resuscitation effort. A minute or so of chest compression also enhances the effectiveness of defibrillation shocks in reviving the patient.

Recently, automatic emergency defibrillators (AED) have been installed in controlled areas such as airplanes, where the presence of trained operators and secure access to the AED can be maintained. The practice of installing AED's in controlled areas is sometimes referred to as Public Access Defibrillation. However, laws in most jurisdictions forbid installation of the devices without maintenance of a number of trained operators in the controlled area and oversight of the program maintenance by a doctor.

Our co-pending application Ser. No. 09/100,840 provides a control system for operating an automatic defibrillator and an automatic chest compression device in coordination with each other to enhance the effectiveness of the resuscitation. The device also provides electro-stimulation for electroventilation, electrocounterpulsion, abdominal binding and glottic closure, all coordinated with the chest compression device to effect electrostimulation at various points in the compression cycle.

SUMMARY

The public access CPR and AED device described below is intended to be installed in public areas where access is readily available to bystanders, first responders, EMT's and doctors. However, it is not necessary, nor desirable, to permit full access of the device to the entire range of people who might desire or require access since some users will not be properly trained to supervise the device's operation. To control and thus permit the optimal degree of access to the system, a tiered access system is used to control physical access and functional enablement of the system. Physical access means access to the device itself, and/or access to certain accessories used for patient treatment in conjunction with the device that may be stored in the device or with the device (ET tubes, venous access kits, laryngoscopes, drugs, etc.). Functional enablement refers to the system allowing operation of certain functions, such as chest compression, alteration of setpoints, application of defibrillating shock, etc. Thus, the system must be told (or determine for itself) that it is permitted to initiate a therapeutic mode before it does so. One mechanism for differentiating the type of user accessing the device is through the identification subsystem sensors, since, for example, only trained personnel are "key holders" (as described in further detail below in reference to FIG. 2.)

The intended models of use for these systems include installation in hospitals and ambulances, and widespread installation in public areas such as workplaces, shopping centers, athletic facilities and stadiums, and even in homes of patients with an identified high risk of cardiac arrest. The devices may be installed in hospitals and ambulances without concern about the level of training for the expected user, because the expected user will be a highly trained operator such as a physician, nurse or emergency medical technician. These trained users can be expected or required to have the expertise necessary to supervise and administer all phases of the resuscitation protocol. However, because installation and activation within minutes of the onset of cardiac arrest is critical to saving a patient's life, it is desirable to allow the device to be deployed by untrained bystanders or minimally trained first responders, and permit trained first responders and untrained bystanders to operate the device in safe modes. The system reserves physical access to advanced equipment and/or functional enablement of advanced modes which may present some danger to the patient for trained first responders. The system may have additional treatment modules, such as drug delivery equipment, that should only be used by expert operators, and the system prohibits access to these modules to all but identified expert operators. Trained first responders and expert operators may identify themselves to the system through the use of access cards, identification numbers or access codes, while the system may assume lack of identification indicates use by an untrained bystander. In all instances of use, the system initiates communications with a remote medical center, where operator identity may be confirmed and the level of access and enablement of the system may be adjusted remotely.

DETAILED DESCRIPTION OF THE INVENTIONS

Figure 1:
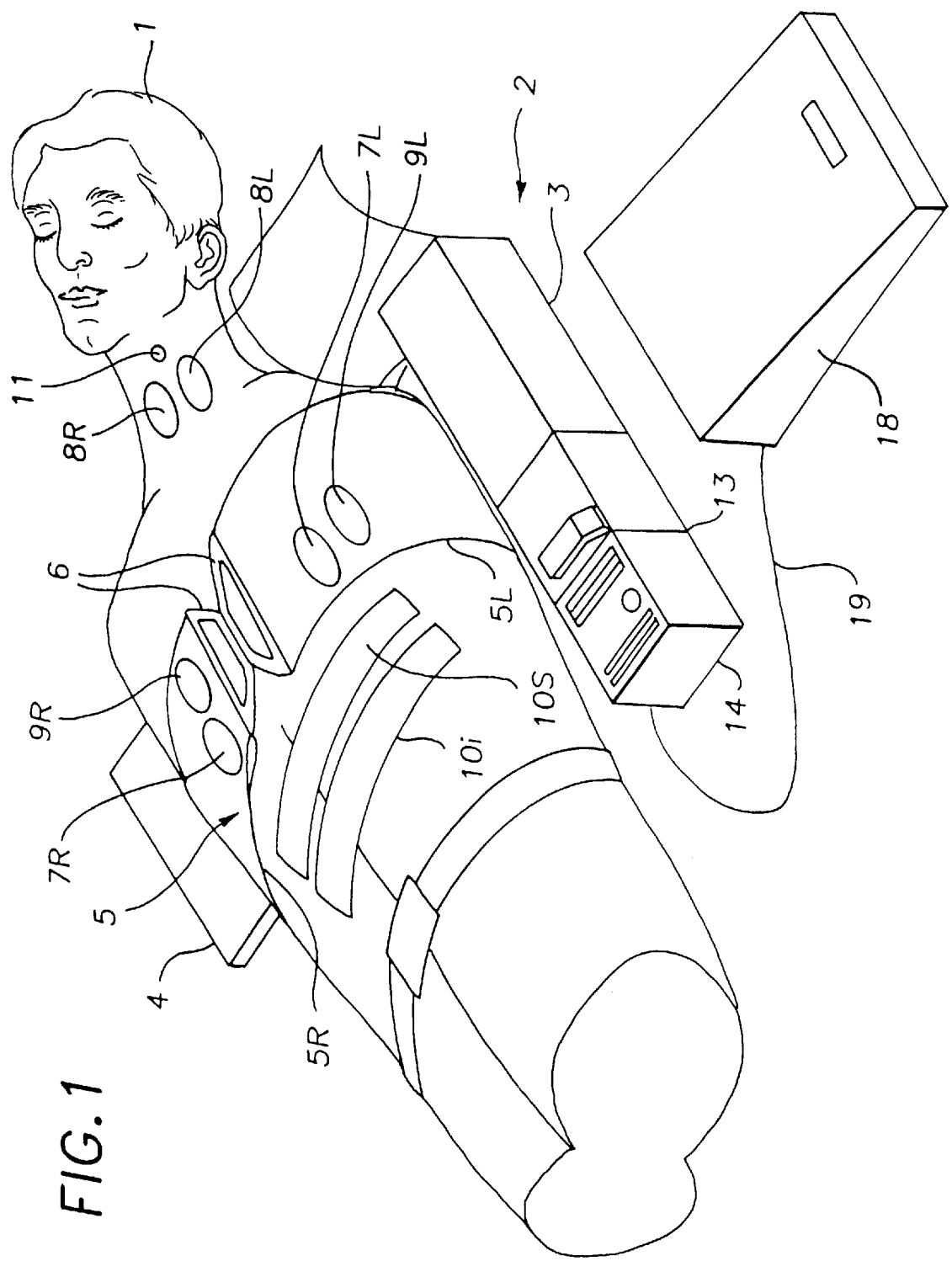
FIG. 1 is diagram of a chest compression, ventilation and defibrillation device controlled by the tiered access system.

FIG. 1 shows the Public Access CPR and AED Device mounted on a patient 1 and ready for use. The chest compression subsystem 2 comprises the motor box 3, the belt cartridge 4, and the compression belt 5 with left and right portions 5L and 5R. The belt is fastened around the patient with fasteners 6 (which may be buckles, Velcro™ hook and loop fasteners or other fasteners with sensors to sense when the belt is fastened). Ventilation electrodes 7L and 7R are mounted on the belts in the area of the lower chest and placed bilaterally over the diaphragm. Bipolar electrodes 8L and 8R (or electrode pairs) may also be placed on the neck, bilaterally, to stimulate the phrenic nerve which courses downwardly through the neck. Defibrillation electrodes 9R and 9L are placed on the right and left sides of the chest and they may also be located below the patient, on the spine between the shoulder blades, and on the center of the chest, respectively. These electrodes are used for establishing the electrical contact needed for EKG sensing, and also for defibrillating the patient. Counterpulsion electrodes 10i and 10s are placed on the skin over the abdominal or rectus muscles, with a line of positive electrodes placed in the superior position and a line of ground electrodes placed in the inferior position. Glottic control electrodes are disposed on an electrode patch 11 placed on the neck along the tracheo-esophageal groove.

The control box 12 houses a computer system that controls the various functions of the device. The computer system controls operation of the chest compression device, acquisition of signals from various feedback mechanisms such as the EKG electrodes, and application of stimulating or defibrillation pulses to the electrodes. (Commercially available sensors, electrodes and EKG analysis systems such as the ForeRunner™ AED sold by HP Heartstream can be used as the basis for the cardioverting subsystem). The computer system may also control operation of additional therapeutic modules, such as drug injection modules. The computer system also controls the communications subsystem 13 used to initiate and maintain communication with a remote medical facility. The communications subsystem may include a telephone handset, keypad and display.

An identification subsystem 14 is operably connected to the control box 12 and/or communication subsystem, 13 and may include a key card reader 15 for reading an encoded card, a keyboard or touchpad 16 for entry of an access code or personal identification number, and a biometric sensor 17 for reading a biometric parameter of the user such as a fingerprint. A secure device enclosure 18 is connected to the control box through electronic cable 19, and is locked or unlocked as controlled by the computer system. The secure device enclosure may house ventilation equipment such as bag valve masks or ventilation tubes, medication used in the ACLS protocol, invasive devices such as intravenous needles (and, if desired, defibrillation electrodes). The system also includes diagnostic devices for sensing EKG, pulse, respiration and temperature. Thus, the system includes several means for resuscitation of the patient and several means for sensing biological parameters of the patient to diagnose the patient. Any number of medical devices, including resuscitation devices and diagnostic devices, may be employed in the system.

The Public Access CPR and AED Device illustrated in FIG. 1 compresses the chest to force blood circulation; stimulates the patient's nerves to cause an inhaling contraction of the diaphragm, the intercostal muscles, and the abdominal muscles; stimulates the patient's abdominal muscles to cause binding or counterpulsile contraction of the abdomen; and delivers defibrillating electrical shock to the patient. The computer system controls all of these therapeutic modes, subject to initialization and enablement of these actions by the operator or remote medical center.

The device is intended to be installed in public areas where access is readily available to bystanders, first responders, EMT's and doctors. The device should be quickly installed on a heart attack victim, prior to the arrival of specially trained users. However, it is not necessary, nor desirable, to permit full access of the device to the entire range of people who might desire or require access since some users will not be properly trained to supervise the device's operation. To control and thus permit the optimal degree of access to the system, a tiered access system is used to control physical access and functional enablement of the system. Physical access means access to the device itself, and/or access to certain accessories used for patient treatment in conjunction with the device that may be stored in the device or with the device (ET tubes, venous access kits, laryngoscopes, drugs, etc.). Functional enablement refers to the system allowing operation of certain functions, such as chest compression, alteration of setpoints, application of defibrillating shock, etc. The system must be told (or determine for itself) that it is permitted to initiate a therapeutic mode before it does so. One mechanism for differentiating the type of user accessing the device is through the identification subsystem sensors, since, for example, only trained personnel are "key holders" (as described in further detail below in reference to FIG. 3.)

The system utilizes a remote medical facility (not shown). The medical facility may maintain a database that stores user identification information, an indication of the user's permitted level of access, and the user's authentication information.

Figure 2:
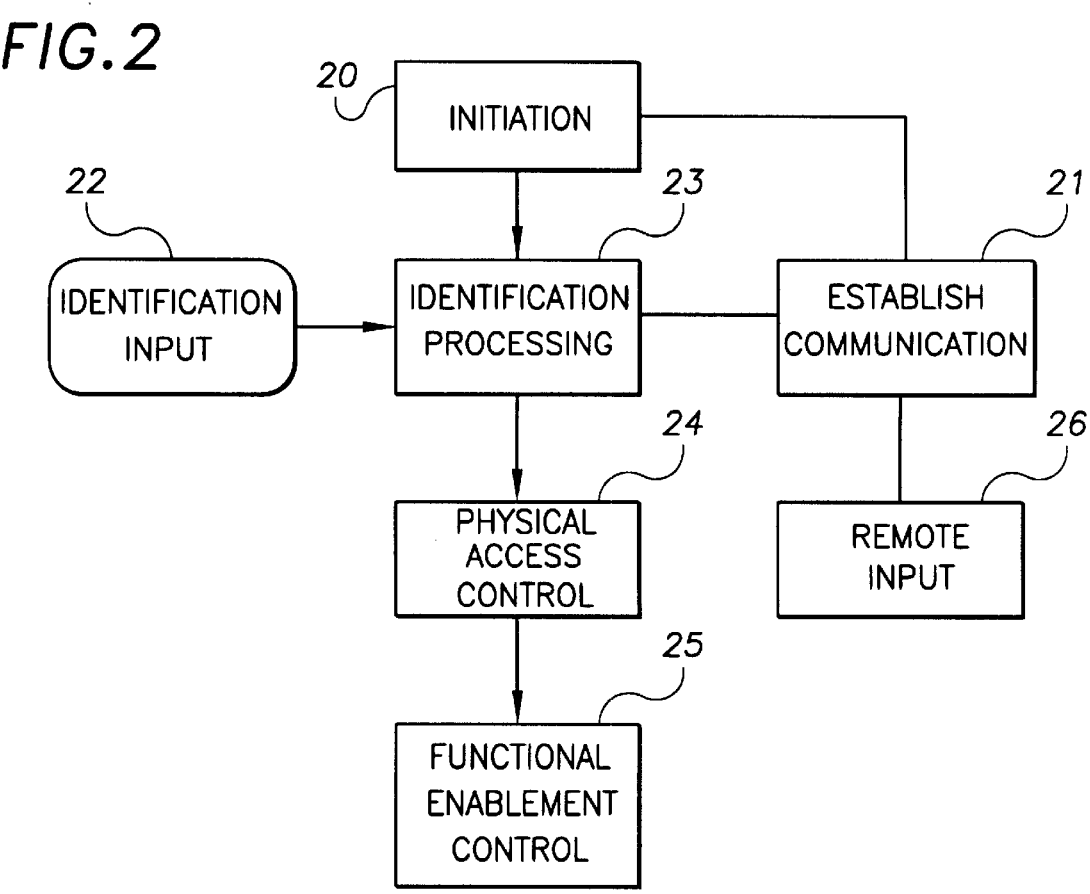
FIG. 2 is a block diagram of the system for controlling access to a resuscitation device.

FIG. 2 illustrates the overall system functions. The initialization module 20 waits for user input that indicates the system is in use and must begin operation. Once the device is accessed, the initialization module operates to start several modules. The system establishes communications with a remote medical facility through the communications module 21. During use, the system will accept user identification information, as indicated by the user identification input module 22. The system analyzes the user's identification, input from a remote medical facility if available, in the identification processing module 23. The system utilizes the user's identity to determine whether or not a user will be allowed physical access to the device, as indicated by the physical access module 24. The system also uses the user's identity to determine which of the various capabilities of the system will be enabled, as indicated by the functional enablement module 25. The remote input module 26 receives input from a remote medical facility, and this input can be used to control the resuscitation devices.

Figures 1, 3A:
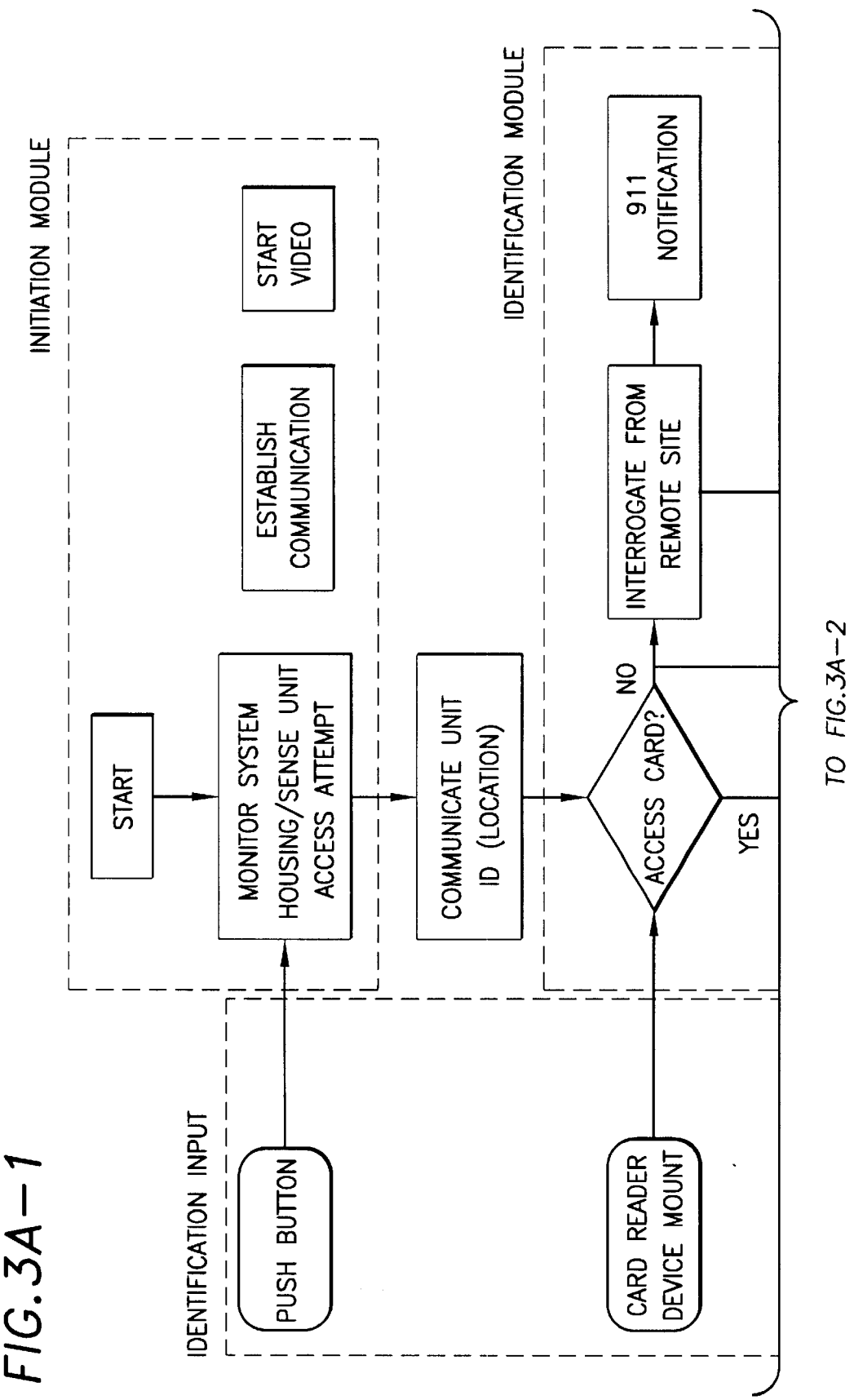
FIGS. 3A and 3B show the system flow chart for system of FIG. 2, with details of the tiered access system.
Figures 2, 3A:
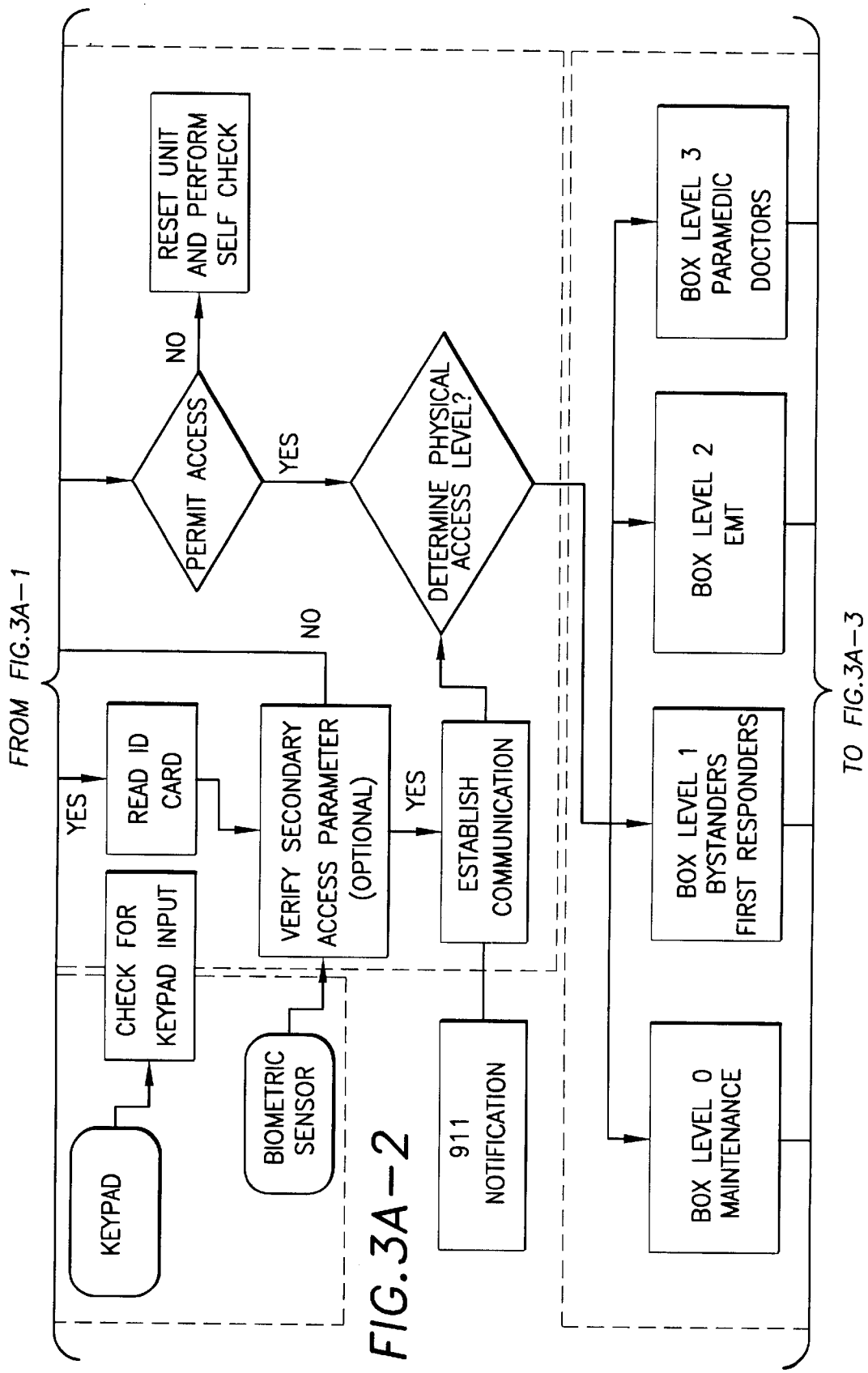
Figures 3, 3B:
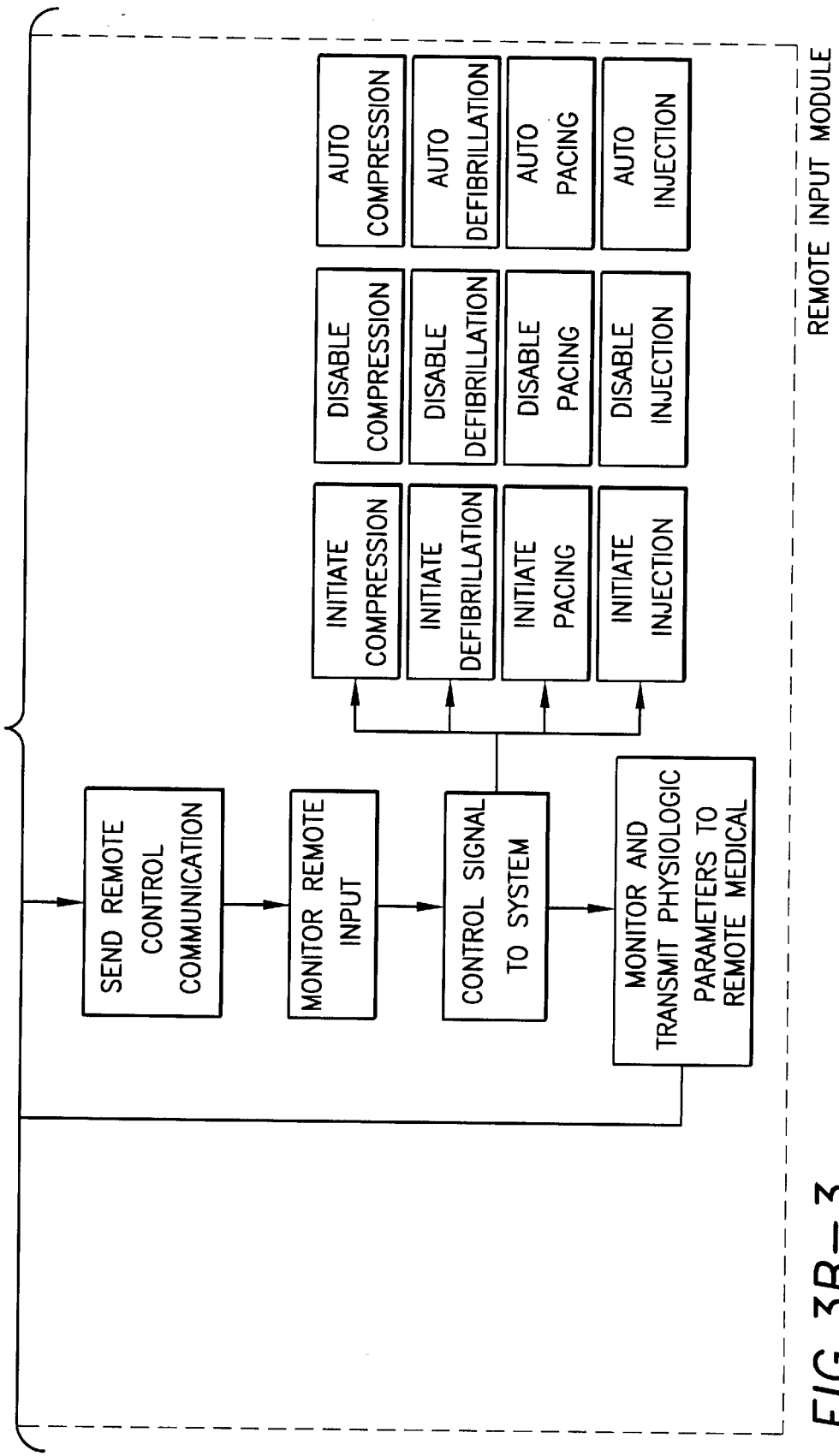

FIGS. 3A and 3B show the system flow chart for system of FIG. 2, with details of the tiered access system. The initialization module 20 achieves the system's ready state. The device is intended to be stored for extended periods of time before it is used, thus making it impractical to keep the computerized components fully operational at all times and the system in constant communication with a remote medical facility. Thus, whenever the system is used, it must be started up so that the various subsystems can achieve a ready state. The system can be designed to start up as any computerized system, either from a completely un-powered condition or from a sleep mode, in which the computer control module is always energized to the extent necessary to sense an input (comparable to a lap-top computer in sleep mode).

The initialization module monitors the system housing to sense a unit access attempt. This is also known as an initiating event, such as the removal of the device from a storage location, disconnection from a charging battery holder, insertion of a key card into the card reader, or operation of any startup sequence initiated by the operator (pushing a button, entering an access code, etc). FIGS. 3A and 3B illustrates an embodiment of the system which uses insertion of a key card (for trained users) as one initiating event, and a push button or telephone pick up (for bystanders) as an alternate initiating event.

Upon recognition of the initiating event, in addition to the steps taken in the CPR protocol as illustrated in our prior patents, the initialization module establishes a communication link with a remote medical facility. Via this link, the initialization module communicates the activation attempt to the medical facility, and differentiates to the medical facility the type of initiating event (physical removal of the device versus insertion of a key card). In this way, the medical facility is made aware of the device activation as well as the type of user activating the device.

The initialization module also communicates an encrypted device ID to the remote medical facility such that the remote medical facility will know where to send trained EMTs. The initialization module also optionally activates an associated video camera system.

The user identification module 22 seeks input from the identification subsystem 14. The identification subsystem may include a key card reader 15, an access code system (touchpad) 16, or mechanical key system (not shown). In this manner, operators of different training levels may be issued a key card, security code, or actual key, so that these trained operators can identify themselves to the system as "key holders". Several levels of access may be provided by use of several "keys," each issued to different levels of trained users and each accepted by the system as identification of a different level of trained user. This provides for the "tiered" access system.

The identification subsystem 14 may also include an optional biometric sensor 17 for use in coordination with a key card reader, using both the biometric information on the key card and the sensed biometric information to ensure the user's identity, and using the training information on the key card to determine the appropriate access to the device.

The identification subsystem 14 is mounted on the resuscitation device, and while the resuscitation device is mounted in the wall mount, it is also detachably wired to the wall mount (through releasable communications cables and connectors) so that it can communicate with any electronic or communications equipment housed within the wall mount. The identification subsystem is thereby carried with the resuscitation device after the system has permitted the device to be detached from the wall mount.

The user identification module monitors the system waiting to sense an input from the identification subsystem 14. If the user identification module senses a key card, access code, or mechanical key, the module reads, for example, the key card identification and communicates to the remote medical facility this information for the next step of determining the physical access level attainable.

If the user identification module does not sense a key card, access code, mechanical key, or if for some reason the local identification fails, redundancy and backup of the identification system is provided such that the user is interrogated by the remote medical facility to ensure that the device is intended to be used for a cardiac arrest victim. This may be necessary when a trained first responder or expert user is available to supervise and operate the device, but cannot be identified by the device due to loss of an access card or failure of the identification devices. If local identification fails, the communications subsystem 13 (not shown) may be used to communicate the identification information or backup identification information to the remote medical facility, and access can be granted by remote input into the identification module. The backup information may be personal identifying numbers of the operator, such as a unique access code or a social security number. Thus the user identification module, upon failure of identification, will respond to an access control signal from the remote medical facility. If the interrogation fails to confirm proper use, the device remains locked so that it remains available for an actual emergency. The system is reset and self check performed in anticipation of an actual emergency.

A concern with such a device is that it might be used by unauthorized users wrongfully in possession of a key. To avoid this possibility, the system can require redundant identification information, which can be provided through biometric sensors. Trained users are issued a magnetic strip card which stores the users training level and access level, along with additional authenticating information. At the very least, the authenticating information may be a personal identification number or PIN, which a user may enter through the keyboard after inserting the access card into the card reader. However, since some trained users may not use the system often enough to ensure that they will remember a PIN, a biometric sensor such as a fingerprint reader may be used. Trained users are issued a key comprising an access card capable of storing biometric information such as the user's fingerprint (retinal scan information, voice print, or other biometric data can be used). The purpose of the biometric data is to provide authentication with information that is guaranteed to be readily available to the user, and cannot be forgotten or lost. The access card may be a credit card sized card with a magnetic strip which contains the users identification, an indication of the users training level, and a representation of the users fingerprint, or unique fingerprint information. These access cards are then used in conjunction with an identification module which includes a card reader and determines the card users training level and recorded fingerprint information, and also includes a fingerprint reader which reads the users fingerprint and compares it with the recorded fingerprint information to ensure that the user is actually the trained user previously identified by a system oversight facility. The system oversight facility can issue the access cards after training the users, thereby maintaining control of the training and the access card. Using this system, there is no need for communication with the system oversight facility, and no need to refer to an extensive database of user identification information or biometric information, so that the material requirements for the identification module are eased. Biometric sensors which read and verify card-stored fingerprints are commercially available.

As illustrated in FIG. 3A, the user identification module 22 refers to the physical access module 24 after the identification process has been completed. If the user is identified as a Level 1 bystander or Level 2 first responder, the physical access module 24 permits access to the device such that it allows the device to be removed from the wall mount (through operation of relay operated locks or other electromechanical locking devices). The device may then be installed on the patient by the bystander. If the user is identified as a level 3 expert operator or EMT, the physical access module may permit access to additional components, such as ACLS supplies (needles/IV/ET tubes) stored within the device or in the wall mount system (again, through operation of electromechanical locks such as electrically operated latches). If the user is identified as a level 4 paramedic or doctor, the physical access module may permit access to drugs. If the user is identified as a level 0 maintenance technician, the system may permit access to the internal workings of the device, such as mechanical components and computer systems to permit service access.

In a large portion of the expected uses, the resuscitation system will be removed from the wall mount by a first operator, typically a bystander. Shortly thereafter, EMT's should arrive on scene. While it is advantageous to the patient to be fitted with the resuscitation device and sensing devices immediately, with the assistance of any available person, it is not necessarily advantageous to permit the system to operate treatment devices which apply power to the body until more experienced operators such as EMT's arrive on scene. Thus, the user identification module is designed so that operators arriving on scene after deployment of the system can enter their identification information, and the system will functionally enable power emitting medical devices and permit physical access to advanced equipment. When EMT's do arrive, communications with a remote medical facility should already be established by the system through the initialization module. The EMT can enter his identification information, which can be processed by the onboard operating system or by the remote medical facility, and either the onboard operating system or the remote medical facility can functionally enable power applying devices. The system may be redundant in its enablement capabilities, allowing enablement by either the remote medical facility or by the local operator (of appropriate level), so that enablement in proper situations is ensured by one or the other (i.e., in case of a communications failure with the remote medical facility).

The physical access module also provides for redundancy and backup where, after the EMT, paramedic, or doctor have arrived on the scene after an initial bystander access, the module monitors the device to sense a key card reader insertion or other access such that the next level of care may be achieved. Essentially, the physical access module is in constant contact with the user identification module to perform this system update.

After the physical access module completes its task (or in parallel to the operation of the physical access module), the system refers to the functional enablement module 25 illustrated in FIG. 3B. This module enables different parts of the control system depending on the access level indicated by the identification module. We have illustrated in the flow chart an initial assignment of functional access which may change according to experience, medical indications and legal requirements at the time the device is used.

Where the user is identified as a level 1 bystander, indicating an untrained user, the system will permit deployment of the device and use of the communications and sensing modules. For example, the system will allow the entire device to be removed from a storage base into which it is normally locked when not in use so that it may be transported to a patient. The system will not allow compression, defibrillation, electrostimulation, access to stored medication, etc. when the user is identified as a level 1 bystander. This is represented by Level 1 in FIG. 3B.

Where the user is identified as a level 2 trained first responder, the system will permit use of the communications modules, sensing modules, compression modules and electrostimulation modules. The system permits all the actions of the level 1 (bystander level), and additionally enables compression. This is identified as Level 2 in FIG. 3B. Compression may be enabled in an automatic mode, meaning that it commences as soon as proper installation of the compression belt is verified by the system, or it may be enabled such that compression commences when the user directs the system to commence compression with user input from the keypad.

Where the user is identifies as a level 3 expert operator or EMT, all the previous modules will be enabled and other more sensitive modules such as the defibrillation module may be enabled, and sensitive adjuncts such as the drug injection devices and invasive sensing devices may be unlocked or enabled. The precise allocation of therapeutic modules to different access levels may vary as experience with the device indicates that therapeutic modules require more or less stringent controls. This is labeled as Level 3 in FIG. 3B.

Finally, where the user is identified as a doctor, the system enables all therapeutic modes (such as ACLS drug delivery, pacing, etc.), and allows the doctor to adjust system thresholds and parameters (such as maximum chest compression, compression rate, defibrillation power, etc.) This is labeled as Level 4 in the flow chart.

All levels provide for a dispatch of appropriate emergency personnel. All levels provide a communication, instruct and monitor deployment function. All levels provide for monitoring and transmitting of physiological parameters (heartbeat, EKG, blood pressure, etc) to the remote medical facility. Finally, all levels provide communication modules so that the system may transmit the physiological data to the remote medical facility. It should be appreciated that the assignment of physical access and functional enablement levels to the different classes of users may vary considerably, and that therapeutic devices may be added to the system in addition to the devices used to illustrate the invention. For example, we expect that operation of the chest compression device will prove to have little adverse effect if applied to a patient who is not suffering from cardiac arrest, so that application of chest compression may be permitted when the device is used by a level 1 bystander.

The remote input module allows the remote medical facility to remain in the loop and control the operation in the field. The remote medical facility receives data via the functional access module. The remote facility may then analyze the data and send remote control communication to the field. For example, the remote medical facility may transmit signals via the feedback module to the device to enable chest compression or other features, as medically indicated by the sensed biological parameters provided by the functional access module.

Figure 4:
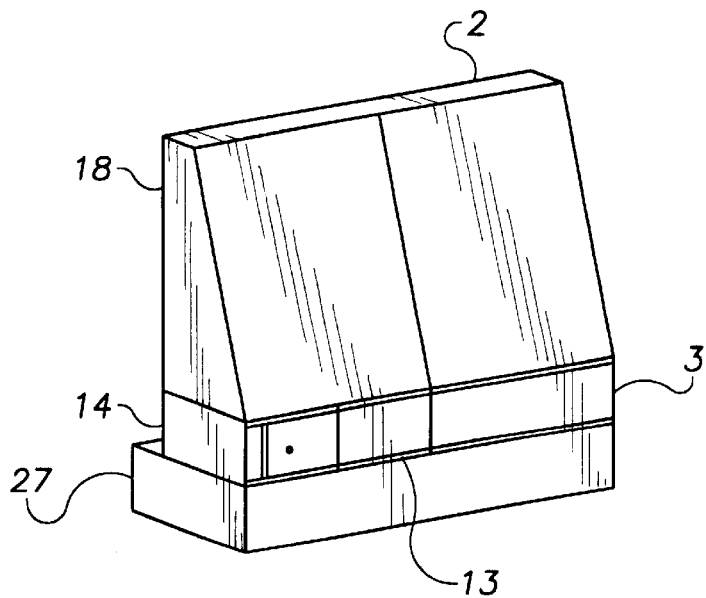
FIG. 4 shows the device of FIG. 1 installed in a locked mounting device.

FIG. 4 shows the resuscitation device configured in a wall mount. The resuscitation device is mounted and locked into a base 27 which is installed in an accessible place where it is likely to be needed, such as in a shopping mall, workplace, theater or stadium. The wall mounted base preferably has a charger for continuously charging the batteries required by the resuscitation system and telephone connections if the system is to be implemented through cordless telephone communication between the device and the remote medical facility (with the cordless telephone base incorporated into the base). The motor box 3, communications module 13, identification module 14 rest in the base, and are locked in the base when the system is not in use. The card reader 15 and telephone handset remain accessible to any potential user, so that the system can be initiated whenever desired. The chest compression subsystem and secure device box remain closed and locked with electromechanical locks. Thus, the device is secured in the base until needed. When needed, the device can be removed from the base in the several ways described above. A trained first responder with an access card may insert the card into the card reader, and this will unlock the entire device from the base so that it can be carried to a heart attack victim. An untrained bystander can initiate communications with the remote medical facility with the telephone handset, and upon interrogation and confirmation of the bystanders need for the device, the device may be unlocked through the transmission of an appropriate signal from the remote medical facility.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A medical system for use on a patient, wherein said medical system requires an operator for use upon the patient, the operator having an operator's predetermined permitted level of access, said medical system comprising:

a chest compression device for compressing the chest of the patient and a defibrillator for providing defibrillating shock to the patient, wherein both the chest compression device and the defibrillator are capable of being either functionally enabled or functionally disabled depending upon the operator's predetermined permitted level of access;

identification means for identifying the operator of the medical system, said identification means comprising an identification card and a card reader, wherein said identification card stores identification information pertaining to the operator's predetermined permitted level of access; and controlling means for controlling the chest compression device and the defibrillator in response to the indication of the operator's predetermined permitted level of access as read from the identification card, wherein the controlling means is capable of permitting physical access to both the chest compression device and the defibrillator depending on the operator's predetermined level of access and the controlling means is capable of functionally enabling at least one of the chest compression device and the defibrillator and functionally disabling at least one of chest compression device and the defibrillator depending upon the operator's predetermined permitted level of access.

2. A medical system for use on a patient, wherein said medical system requires an operator for use upon the patient, said medical system comprising:

a chest compression device for compressing the chest of the patient and a defibrillator for providing defibrillating shock to the patient, wherein both the chest compression device and the defibrillator are capable of being either functionally enabled or functionally disabled depending upon the operator's predetermined permitted level of access;

identification means for identifying the operator of the medical system, said identification means comprising an identification card and a card reader, wherein said identification card stores identification information pertaining to the operator, an indication of the operator's predetermined permitted level of access, and authentication information for the operator;

means for entering authentication information into the identification means for comparison with the authentication information stored on the identification card; and controlling means for controlling the chest compression device and the defibrillator in response to the indication of the operator's permitted level of access as read from the identification card, wherein the controlling means is capable of permitting physical access to both the chest compression device and the defibrillator depending on the operator's predetermined level of access and the controlling means is capable of functionally enabling at least one of the chest compression device and the defibrillator and functionally disabling at least one of chest compression device and the defibrillator depending upon the operator's predetermined permitted level of access.

3. A resuscitation system for use on a patient, wherein said resuscitation system requires an operator for deployment on the patient, and the system may be operated by various classes of operators assigned varying levels of access, said resuscitation system comprising:

a chest compression device having a belt;

defibrillation electrodes, attached to the belt, for supplying a defibrillating shock to the patient;

identification means for identifying an operator of the system for determining the operator's permitted level of access; and a computer for functionally enabling or disabling the compression device and the defibrillation electrodes in response to the operator's permitted level of access, wherein the computer is programmed to determine an operators permitted level of access, to permit the compression device to be placed on the patient and permit operation of the compression device when the compression device is placed on the patient regardless of the operator's permitted level of access; and the computer is further programmed to permit placement of the defibrillation electrodes onto the patient regardless of the operator's permitted level of access and to prohibit delivery of shock through the defibrillation electrodes for operators identified as having a first permitted level of access and to allow delivery of shock through the defibrillation electrodes for operators identified as having a second permitted level of access.

* * * * *